(12) United States Patent
Ryotokuji

(10) Patent No.: US 11,173,273 B2
(45) Date of Patent: Nov. 16, 2021

(54) STIMULATION APPLICATION APPARATUS

(71) Applicant: Kenji Ryotokuji, Chiba (JP)

(72) Inventor: Kenji Ryotokuji, Chiba (JP)

( * ) Notice: Subject to any disclaimer, the term of this patent is extended or adjusted under 35 U.S.C. 154(b) by 234 days.

(21) Appl. No.: 15/366,534

(22) Filed: Dec. 1, 2016

(65) Prior Publication Data

US 2017/0274173 A1 Sep. 28, 2017

Related U.S. Application Data

(63) Continuation-in-part of application No. 15/220,992, filed on Jul. 27, 2016, now abandoned, which is a
(Continued)

(51) Int. Cl.
*A61M 21/02* (2006.01)
*A61H 39/06* (2006.01)
(Continued)

(52) U.S. Cl.
CPC .............. *A61M 21/02* (2013.01); *A61F 7/007* (2013.01); *A61H 39/04* (2013.01); *A61H 39/06* (2013.01); *A61H 39/08* (2013.01); *A61F 2007/0096* (2013.01); *A61H 2201/0207* (2013.01); *A61H 2201/0221* (2013.01); *A61H 2201/10* (2013.01); *A61H 2201/169* (2013.01); *A61H 2201/5007* (2013.01); *A61H 2201/5092* (2013.01); *A61H 2205/125* (2013.01); *A61H 2209/00* (2013.01); *A61H 2230/255* (2013.01);
(Continued)

(58) Field of Classification Search
CPC ....... A61H 39/04; A61H 39/06; A61N 5/0619
See application file for complete search history.

(56) References Cited

U.S. PATENT DOCUMENTS 4,126,128 A * 11/1978 Takahashi .............. A61H 39/06
601/19
5,284,272 A * 2/1994 Wei .......................... A61H 7/00
222/192
(Continued)

OTHER PUBLICATIONS

Non-Final Office Action dated Mar. 20, 2015, issued in U.S. Appl. No. 13/551,730 (10 pages).
(Continued)

*Primary Examiner* — Kaitlyn E Smith
(74) *Attorney, Agent, or Firm* — Westerman, Hattori, Daniels & Adrian, LLP

(57) ABSTRACT

A stimulation application apparatus includes a substrate, a stimulation application member provided on one surface of the substrate to apply a stimulation to a site, and a stimulation imposition layer provided on another surface of the substrate opposed to the first surface to impose the stimulation. The site includes at least one area selected from a group of (F) site that intersects the perpendicular line of the medial malleolus on an extension line of the medial margin on os metatarsale primam 1 and 2 in foot sole, and (L) incisurasive foramen supraorbitalis site, and (K) site where the lintersection of the line connecting an augulus oculi medialis of eye and L site, and perpendicular of an augulus oculi lateralis of eye is located, and (M) site of augulus oculi lateralis located above 1 horizontal finger from center of the line where connect the inner end of left and right eyebrow.

6 Claims, 8 Drawing Sheets
(1 of 8 Drawing Sheet(s) Filed in Color)

Related U.S. Application Data continuation-in-part of application No. 15/078,533, filed on Mar. 23, 2016, now Pat. No. 10,828,188.

(51) Int. Cl.
| | | |
|---|---|---|
| *A61H 39/08* | (2006.01) | |
| *A61F 7/00* | (2006.01) | |
| *A61H 39/04* | (2006.01) | |
| *A61M 21/00* | (2006.01) | |
| *A61N 2/00* | (2006.01) | |
| *A61N 5/06* | (2006.01) | |

(52) U.S. Cl.
CPC .......... *A61H 2230/505* (2013.01); *A61M 2021/0022* (2013.01); *A61M 2021/0055* (2013.01); *A61M 2021/0066* (2013.01); *A61M 2205/3368* (2013.01); *A61M 2205/3653* (2013.01); *A61M 2210/086* (2013.01); *A61N 2/006* (2013.01); *A61N 5/0619* (2013.01); *A61N 5/0622* (2013.01)

(56) References Cited

U.S. PATENT DOCUMENTS

| | | | | |
|---|---|---|---|---|
| 5,674,261 | A | | 10/1997 | Smith |
| 5,848,981 | A | * | 12/1998 | Herbranson ............ A61F 7/10 601/134 |
| 5,950,635 | A | | 9/1999 | Garcia-Rill et al. |
| 5,976,547 | A | | 11/1999 | Archer et al. |
| 6,074,411 | A | * | 6/2000 | Lai .................. A61N 5/0619 607/89 |
| 6,256,539 | B1 | | 7/2001 | Swing |
| 6,454,732 | B1 | * | 9/2002 | Lee .................. A61F 7/00 601/101 |
| 8,932,198 | B1 | * | 1/2015 | You .................. A61B 17/545 600/27 |
| 9,649,244 | B1 | * | 5/2017 | Jacobs .............. A61H 7/003 |
| 9,662,489 | B1 | * | 5/2017 | Cargill, III .......... A61N 1/322 |
| 10,039,693 | B1 | * | 8/2018 | Hoffman ............. A61H 39/04 |
| 2001/0031989 | A1 | * | 10/2001 | Swing ............... A61N 1/326 607/2 |
| 2002/0082668 | A1 | * | 6/2002 | Ingman ............. A61N 1/20 607/98 |
| 2003/0078637 | A1 | * | 4/2003 | Akita ................ A61N 5/0619 607/88 |
| 2003/0125648 | A1 | * | 7/2003 | Leason ............. A61H 15/0085 601/15 |
| 2003/0163176 | A1 | * | 8/2003 | Bae ................ A61F 7/007 607/96 |
| 2004/0044384 | A1 | | 3/2004 | Leber et al. |
| 2004/0044390 | A1 | * | 3/2004 | Szeles ............... A61H 39/002 607/142 |
| 2004/0088036 | A1 | * | 5/2004 | Gilbert ............. A61H 39/002 607/148 |
| 2004/0102819 | A1 | * | 5/2004 | Zou ................ A61N 1/36021 607/46 |
| 2004/0138712 | A1 | * | 7/2004 | Tamarkin ............ A61N 1/0428 607/3 |
| 2004/0143313 | A1 | * | 7/2004 | Chang ............... A61N 1/0408 607/108 |
| 2004/0230228 | A1 | * | 11/2004 | Nakamura ........... A61N 1/20 607/3 |
| 2004/0230256 | A1 | * | 11/2004 | Lin-Hendel ......... A61H 39/002 607/72 |
| 2005/0033397 | A1 | * | 2/2005 | Aisenbrey ........... A61N 1/0452 607/142 |
| 2005/0043753 | A1 | | 2/2005 | Rabiner et al. |
| 2005/0075530 | A1 | | 4/2005 | Kaizuka |
| 2005/0209537 | A1 | | 9/2005 | Gleason et al. |
| 2006/0085049 | A1 | * | 4/2006 | Cory ................. A61B 5/0536 607/48 |
| 2006/0095109 | A1 | * | 5/2006 | Ming-Daw .......... A61H 39/002 607/148 |
| 2006/0155225 | A1 | * | 7/2006 | Murdock ............ A61H 15/0092 601/131 |
| 2006/0167526 | A1 | * | 7/2006 | Wan ................ A61H 39/002 607/46 |
| 2006/0195168 | A1 | * | 8/2006 | Dunbar .............. A61F 7/007 607/108 |
| 2007/0038275 | A1 | | 2/2007 | Kim |
| 2007/0142891 | A1 | * | 6/2007 | Stanley .............. A61F 7/007 607/144 |
| 2007/0191745 | A1 | * | 8/2007 | Tucker .............. A61H 7/00 601/135 |
| 2007/0277806 | A1 | | 12/2007 | Dodo |
| 2007/0293918 | A1 | * | 12/2007 | Thompson .......... A61N 1/36021 607/72 |
| 2008/0027364 | A1 | * | 1/2008 | Moutray ............. A61H 7/001 601/134 |
| 2008/0029079 | A1 | | 2/2008 | Dodo |
| 2008/0058915 | A1 | * | 3/2008 | Chang .............. A61H 39/002 607/140 |
| 2008/0063736 | A1 | * | 3/2008 | Kim ................. A61H 39/04 424/740 |
| 2008/0228248 | A1 | | 9/2008 | Guyron et al. |
| 2008/0281392 | A1 | * | 11/2008 | Paolizzi ............. A61H 39/002 607/140 |
| 2008/0306507 | A1 | * | 12/2008 | Woodley ............ A61H 39/04 606/204 |
| 2008/0319274 | A1 | * | 12/2008 | Ballegaard .......... A61B 5/00 600/300 |
| 2009/0048547 | A1 | * | 2/2009 | Chen ............... A61H 7/001 601/15 |
| 2009/0132018 | A1 | * | 5/2009 | DiUbaldi ........... A61N 1/0456 607/152 |
| 2009/0157149 | A1 | * | 6/2009 | Wahlgren ........... A61N 1/0456 607/66 |
| 2009/0198310 | A1 | * | 8/2009 | Chen ................ A61F 7/007 607/108 |
| 2009/0287280 | A1 | | 11/2009 | Wong et al. |
| 2010/0004709 | A1 | | 1/2010 | Mische |
| 2010/0036280 | A1 | * | 2/2010 | Ballegaard ......... A61B 5/4035 600/552 |
| 2010/0056848 | A1 | | 3/2010 | Szeto |
| 2010/0069995 | A1 | | 3/2010 | Danielsson |
| 2010/0081973 | A1 | * | 4/2010 | Tsai ................ A61H 15/0078 601/134 |
| 2010/0286577 | A1 | * | 11/2010 | Tsai ................ A61H 15/0078 601/112 |
| 2011/0034782 | A1 | * | 2/2011 | Sugimachi ........... A61H 39/04 600/301 |
| 2011/0106207 | A1 | | 5/2011 | Cauller et al. |
| 2011/0106219 | A1 | | 5/2011 | Cauller et al. |
| 2011/0172749 | A1 | | 7/2011 | Christensen et al. |
| 2011/0306999 | A1 | * | 12/2011 | Lam ................ A61H 39/08 606/189 |
| 2012/0172771 | A1 | * | 7/2012 | Jian ................ A61H 15/0092 601/46 |
| 2012/0247400 | A1 | * | 10/2012 | Hoffmann ........... A01K 13/006 119/850 |
| 2012/0260531 | A1 | * | 10/2012 | Shi ................. A43B 3/0015 36/102 |
| 2013/0041396 | A1 | * | 2/2013 | Ryotokuji ........... A61H 39/04 606/189 |
| 2013/0085426 | A1 | * | 4/2013 | Brodsky ............ A61H 15/00 601/128 |
| 2013/0085484 | A1 | * | 4/2013 | Van Valen .......... A61B 18/18 606/6 |
| 2013/0137992 | A1 | | 5/2013 | Yamazaki et al. |
| 2013/0138143 | A1 | * | 5/2013 | Chechelnitsky ....... A61H 39/04 606/204 |
| 2013/0171232 | A1 | | 7/2013 | You |
| 2013/0172967 | A1 | | 7/2013 | You |
| 2013/0172969 | A1 | | 7/2013 | You |
| 2013/0172970 | A1 | | 7/2013 | You |
| 2013/0281894 | A1 | * | 10/2013 | Ling ................ A61H 15/00 601/19 |
| 2014/0200544 | A1 | | 7/2014 | Ryotokuji |

(56) References Cited

U.S. PATENT DOCUMENTS

| | | | |
|---|---|---|---|
| 2014/0330336 A1* | 11/2014 | Errico | A61N 1/36021 607/45 |
| 2014/0343599 A1* | 11/2014 | Smith | A61B 17/1327 606/202 |
| 2015/0018717 A1* | 1/2015 | Lyons | A61H 39/02 600/587 |
| 2015/0297909 A1* | 10/2015 | Peashock | A61N 2/002 600/13 |
| 2016/0158099 A1* | 6/2016 | Kupferman | A61H 39/04 606/204 |
| 2016/0184173 A1* | 6/2016 | Chen | A61H 7/007 601/18 |
| 2016/0270479 A1* | 9/2016 | Suzuki | A43B 11/00 |
| 2016/0317387 A1* | 11/2016 | Cox | A61H 39/04 |
| 2016/0331070 A1* | 11/2016 | Williams P.D.M. | A43B 7/146 |
| 2016/0367434 A1* | 12/2016 | Gruber | A61H 39/002 |
| 2017/0319844 A1* | 11/2017 | Woo | A61N 1/04 |
| 2017/0326028 A1* | 11/2017 | Doogan | A61H 39/04 |
| 2018/0055728 A1* | 3/2018 | Lee | A61H 39/06 |

OTHER PUBLICATIONS

Non-Final Office Action dated Sep. 15, 2015, issued in U.S. Appl. No. 13/551,730 (9 pages).

* cited by examiner

First

```
10:00     :05      :10      :15      :20                    :35        :45
          rest supine position
          measurement 1      blood sampling 1    stimulation   measurement 2
```

Second

```
10:00     :05      :10      :15      :20
          rest supine position
          measurement 3      blood sampling 2
```

FIG. 9A

| Sample | H | C | BP | B2 |
|---|---|---|---|---|
| Thickness | 1.5 | 1.5 | 1.5 | 2.0 |

Surgical tape having samples thereon (in a view from the sided to be attached)

STIMULATION APPLICATION APPARATUS

CROSS-REFERENCES TO RELATED APPLICATION

This patent application is a continuation-in-part of U.S. application Ser. No. 15/220,992, which is a continuation-in-part of U.S. application Ser. No. 15/078,533, now U.S. Pat. No. 10,828,188, filed filed Mar. 23, 2016, which is a continuation-in-part of U.S. application Ser. No. 13/551,730, now U.S. Pat. No. 9,358,180, filed filed Jul. 18, 2012, which claim priority to U.S. Provisional Application No. 61/508,883 filed Jul. 18, 2011, U.S. Provisional Application No. 61/526,089 filed Aug. 22, 2011, and U.S. Provisional Application No. 61/635,359 filed Apr. 19, 2012, the contents of which are incorporated herein by reference in their entireties.

BACKGROUND

Technical Field

The present invention relates to a stimulation application apparatus for performing a stimulus method in which stress is released in order to improve lifestyle-related diseases such as the diabetes, obesity and high blood pressure resulting from the stress, by activating a peripheral circulatory function and an autonomic nervous function through a stimulus to specific parts of a body surface by an acupuncture needle(s) or heating etc. thereby releasing the stress, and a stress-free medical treatment method based on the stimulus method.

Related Art

U.S. Pat. No. 5,950,635 discloses a point surface stimulus method according to a specific acupuncture treatment for reducing anxiousness, for example, stress. The patent discloses that LR3, HT3, and PC6 are specified as stimulus points of patients. Electrodes are brought into contact with these three stimulus points, respectively, thereby passing current through the electrode. Here, the LR3 is located on the top of the foot, at 2 cm proximal to the margin of the first and second toes. The HT3 is located on the inside of each elbow, midway between the medial end of an elbow crease and the medial epi-condyle of the humerus when the elbow is fully flexed. The PC6 is located on each wrist, 2 cm proximal to the midpoint of the wrist crease between the tendons of the palmaris longus and the flexor carpi radialis muscle. In the patent, a P1 potential is focused on with respect to at least one subcortical source, specifically in the pedunculopontine nucles (PPN), the chlinergic arm of the reticular activating system. That is, the patent discloses that when the above-mentioned stimulus points (LR3, HT3, and PC6) are stimulated with needles, the P1 potential decreases and anxiousness is reduced. In addition, other than the stimulus points LR3, HT3, and PC6, no stimulus points to be stimulated with the needles are disclosed. However, the patent discloses that, focusing on pedunculopontine nucles (PPN), anxiousness is reduced due to a decrease of the P1 potential. However, it does not discloses that due to reduction of anxiousness, it is possible to achieve effects, such as normalization of blood pressure, degression of stress, rise in body temperature, degression of neutral fat, degression of cholesterol, and an improvement of a blood sugar level due to relief of insulin resistance.

SUMMARY

By earnest research work, the present inventor found out a specific area to be stimulated, at which diabetes resulting from stress, and lifestyle-related diseases such as obesity and high blood pressure can be improved by making psychological stress free by a stimulus through acupuncture needles or heating to specific area to be stimulated of a body surface.

It is an object of the present invention to offer a body surface stimulus method for releasing psychological stress, in which stress is made free by activating a peripheral circulatory function and an autonomic nervous function by applying acupuncture needles to specific area to be stimulated of a body surface, or a stimulus based on heating etc., so that a symptom of diabetes resulting from the stress and a symptom of lifestyle-related disease such as obesity and high blood pressure may be improved.

It is another object of the present invention to offer a stress-free treatment using the body surface stimulus method for releasing the psychological stress. According to the present invention, since a specific area to be stimulated of a body surface by acupuncture needles or heating etc. affects a homeostatic function (nerve, immunity, and endocrine system) though a peripheral circulatory function and autonomic nerves, it is possible to obtain effects, such as a normalization of blood pressure, a reduction of stress, a rise in body temperature, a degression of neutral fat, a degression of cholesterol, and an improvement of a blood sugar level due to relief of insulin resistance.

In the present invention, stimuli are, non-simultaneously and independently from each other, applied to at least one area selected according to the condition of disease, thereby achieving a reduction of psychological stress, a rise in core body temperature, a reduction of neutral fat, a reduction of cholesterol, an improvement of a blood sugar level by relief of insulin resistance, and suppression of arteriosclerosis. In the present invention, a stimulation of a thermal stimulus pattern, which is formed by controlling an electric type heating apparatus, is non-simultaneously and independently applied to at least one areas selected according to the condition of disease, thereby achieving a reduction of psychological stress, a rise in core body temperature, a reduction of neutral fat, a reduction of cholesterol, an improvement of a blood sugar level by relief of insulin resistance, and suppression of arteriosclerosis.

In another aspect of the present invention, a stimulation application apparatus configured to conduct the methods disclosed in this application is provided. The stimulation application apparatus includes: a substrate; a stimulation application member provided on a first surface of the substrate and configured to apply a stimulation to a site of a body to be stimulated; and a stimulation imposition layer provided on a second surface of the substrate opposed to the first surface and configured to impose the stimulation applied to the site via the stimulation application member. The site includes at least one area selected from a group of (F) site that intersects the perpendicular line of the medial malleolus on an extension line of the medial margin on os metatarsale primam 1 and 2 in foot sole, and (L) incisurasive foramen supraorbitalis site, and (K) site where the lintersection of the line connecting an augulus oculi medialis of eye and L site, and perpendicular of an augulus oculi lateralis of eye is located, and (M) site of augulus oculi lateralis located above 1 horizontal finger from center of the line where connect the inner end of left and right eyebrow.

BRIEF DESCRIPTION OF THE DRAWINGS

Other features and advantages of the present stimulus method for releasing stress, and stress-free medical treatment method by the stimulus method will be apparent from the ensuing description, taken in conjunction with the accompanying drawings. The present application file contains at least one drawing executed in color. Copies of this application publication with color drawings will be provided by the Office upon request and payment of the necessary fee.

FIG. 8A shows one embodiment of the stimulation application apparatus. FIG. 8B shows the stimulation application apparatus provided with an adhesive member 22.

FIGS. 9A and 9B show a comparative test on heat-retaining effects according to the apparatus of FIG. 8. FIG. 9A shows a method for comparing the heat-retaining effects. FIG. 9B shows photographic data showing the results of the comparative test on the heat-retaining effects.

DESCRIPTION

Figure 1:
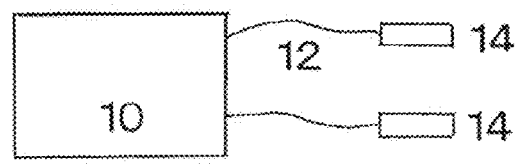
FIG. 1 is a schematic view of an electric type heating apparatus used for the present invention.

In a stimulus treatment method according to the present invention, a stimulus treatment method for providing medical treatment by applying a stimulus to a specific area to be stimulated at a body surface by a stimulus applying apparatus so as to bring an increase rate of blood flow to 60% or more, preferably, 100% or more, wherein the blood flow is measured by a laser Doppler tissue blood flow meter attached to a central part of an inner side of a wrist joint.

The specific area is at least one area selected from a group of os metatarsale primam 1 and 2 interosseous, os metatarsale primam 2 and 3 interosseous, and part that intersects the perpendicular line of the medial malleolus on an extension line of the medial margin on os metatarsale primam 1 and 2 in foot sole of right and left.

The specific area is an area of a near glandula thyreoidea.

The specific area is an area between the outer skin and a horizontal line of the inside boundary part of a hallux distal phalanx bottom and a proximal phalanx bone head in foot sole of right and left.

The stimulus is non-simultaneously and independently applied to at least one areas selected according to a condition of disease.

The stimulus applying apparatus is a heat stimulus applying apparatus, and the heat stimulus applying apparatus forms a warm temperature stimulus pattern, wherein the stimulus pattern is made up of a thermal stimulus waveform and an interval, and the thermal stimulus waveform includes a heating waveform obtained by raising temperature to a peak temperature, 50±5 degrees Celsius by heating, and a heat release waveform formed by stopping the heating when the peak temperature is reached.

The stimulus is selected from an acupuncture needle stimulus, a warm temperature stimulus, an optical stimulus, a magnetic stimulus, and an ultrasonic stimulus.

A stress-free treatment method comprises the stimulus method.

An stimulus evaluation method comprises a stimulus method, wherein the increase rate of the blood flow is used as an indicator of the stimulus evaluation.

In general, two systems will be activated if the stress is applied to a living organism. One of the systems is a sympathetic nervous system beginning at a ceruleus nucleus (locus ceruleus), wherein noradrenalin is secreted from nerve ends, and adrenalin is secreted from adrenal cortex.

The other system is a HPA system (hypothalamus*pituitary*adrenal axis), wherein CRH (corticotropine releasing hormone) secreted from a hypothalamus (nucleus paraventricularis) acts on the hypophysis, and ACTH (adrenocorticotropic hormone) secreted from the pituitary anterior lobe (adenohypophysis) acts on the adrenal cortex, whereby finally glucocorticoid (cortisol) is secreted from the adrenal cortex. The cortisol is considered as an index of mental/physical stress, and can be also measured from saliva. In this stimulus, salivary amylase, ACTH, and cortisol were decreased. It would appear that a normalization of a stress reaction system hormone takes place.

Cortisol controls carbohydrate, fat, and protein metabolism, and is an indispensable hormone for living organisms. Blood pressure and a blood sugar level are raised depending on the quantity thereof secreted by stress, and it affects various living organism functions such as an immune system (inflammatory suppression), that is, for example, causing a decline in the immune function, a blood circulatory system, and a metabolism system (sugar rebirth) (glyconeogenesis). Furthermore, there is a receptor of the cortisol in a hypothalamus, a hippocampus, and a hypophysis, and if the amount of secretion of the cortisol increases, the amount of synthesis of CRH or ACTH decreases. As a result, the cortisol secretion is suppressed. Moreover, in recent years, there have been a report, as an index, based on MRI etc. of the brain of a patient with a PTSD (posttraumatic stress disorder), in which when the cortisol is secreted so much due to excessive stress, it atrophys the hippocampus. Thus, the cortisol also affects a central system (cognition, memory, emotions), and prevention of dementia, etc. can be expected by using an acupuncture needle stimulus.

A substance, which attracts attention together with the cortisol, is DHEA. The DHEA is a steroid hormone secreted from an adrenal cortex as well as the cortisol. It has been reported that the action is opposite to the cortisol. For example, although the cortisol suppresses Th1 immunity activity (NK cells, killer T cells) and facilitates Th2 immunity activity (B cells), DHEA facilitates the Th1 immunity activity conversely. Moreover, it is thought that patients with depression have a high cortisol level and have a low DHEA level, and a ratio thereof (cortisol/DHEA ratio) is important. It is considered that DHEA is a hormone which adjusts an action of the cortisol well.

Moreover, DHEA-sulfate (sulfate group-bound DHEA: DHEAS) (sulfate group bound form) is also thought to be important. Unlike the cortisol, there is no negative feedback as to DHEA, and if it is secreted, it is changed into DHEAS and accumulated, for a comparatively short time. Although the DHEAS itself has no activity as a hormone, the DHEAS is changed into DHEA in an organ which serves as a target, and acts on the target organ. The DHEAS is considered as an index showing a stable state of the DHEA. The DHEA and DHEAS are considered to have relation with stress.

It is considered that there are mechanism due to vasodilatation and mechanism under influence on sympathetic nerves by such stimulus. The action of the dilatation of vessel is considered to increase production of calcitonin gene-related peptide (CGRP) by the stimulus. It is thought that discharge of the CGRP etc. is increased due to an increase in muscle blood flow when nerves etc. are stimulated by the stimulus. Namely, efferent autonomic nerves or motor nerves are not included in a dorsal spinal nerve root. It is thought that axon-reflex mechanism arises due to a stimulus of afferent nerves etc., and CGRP is discharged from an end thereof, and it is based on the mechanism which a blood vessel of a governed area is dilated.

Furthermore, the influence on an autonomic nerve activity, which governs a blood vessel, is also assumed. Blood vessels of muscles are governed by adrenergic sympathetic nerves and cholinergic sympathetic nerves. The former is vasoconstrictor nerves through an alpha-receptor, and the latter is vasodilator nerves through acetylcholine. It is said that even at rest the former always works for the blood vessels of muscle in a state of tonus thereof, so that the blood vessels are always maintained in a coarctation state to some extent. On the other hand, as to the latter, it is thought that unstriped muscles of a blood vessel are relaxed in response to acetylcholine discharged from the end of nerves, so that the blood flow volume increases.

When the stimulus by acupuncture needles or warm temperature heating maintains parasympathetic nerve predominance, a long-term sympathetic nerve sthenia status is improved, so that it is also considered that there is a possibility that suppression of a RA system in a kidney is facilitated. This improves a hypertensive patient's QOL.

Furthermore, continuous stimulus treatment such as acupuncture needles and warm temperature heating showed a tendency of reduced insulin. It is thought that it is based on a continuous improvement of insulin resistance rather than an increase of a temporary insulin secretion. Moreover, obesity is one of the most important risk-factors of IGT. Harris et al. have epidemiologically showed the relation of the IGT and DM, and the obesity, in which that degree of obesity and an increase in weight play a major role in pathogenesis of DM. Therefore, it is thought that an improvement of the obesity problem leads to prevention of DM and also hypertension. In a medical interview, weight reduction of about 2 kg/month on average was confirmed.

Furthermore, in view of a rise in core body temperature and blood pressure change, etc., it is thought that the stimulus of acupuncture needles, warm temperature heating, etc. adjusts the blood flow of each organ through systemic blood pressure and autonomic nerves. It is thought that there is an effect of acupuncture needles, which are exerted on the systemic blood pressure, that an acupuncture needle stimulus causes a reaction to the systemicity through the sympathetic nerves.

A laser Doppler tissue blood flow meter ALF21D (manufactured by Adovans) is used to measure blood flow on a living tissue. In the laser Doppler tissue blood flow meter ALF21D, when a living tissue is irradiated with semiconductor laser light (whose wavelength is 780 nm), light reflected from the tissue is converted into an electric signal and the electric signal is processed, thereby obtaining a information of the blood flow.

A C type laser probe (10 mm in diameter, 3 mm in thickness, 2 $mm^2$ in a laser irradiation area, and 1 mm in measurement depth) of the laser Doppler tissue blood flow meter was attached to a central part of a wrist joint horizontal line, and was measured, taking a 15-minute rest after a stimulus. A warm temperature heating probe is attached between bone heads of second and third metacarpal bones. And from measurement of the blood flow, a increase rate of the blood flow was calculated.

As to the principle of the laser Doppler tissue blood flow, laser light collides with red blood cells, which flow through the inside of a blood vessel, and the Doppler shift (frequency change), which is produced when receiving dispersion, is used. This measurement method is characterized by non-invasive and real time responsiveness and a capability of consecutive measurement. Furthermore, the ALF21D, which was used this time, could display a blood flow on ml/min/100 g scale. This is because signal processing is performed based on the theory of Bonner et al.

Description of the mechanism of an increase in a blood flow in a stress free treatment will be given below. A mental stress to a living body stimulates sympathetic nerves through the cerebral limbic system and hypothalamic pituitary, thereby constricting blood vessels and impairing the microcirculation system including internal organs of the living body. In the "stress free treatment" in response to a blood flow reduction response, a rise in body temperature of peripheral subcutaneous part at distances of 3 mm and 5 mm and, secretion control of stress hormone (amylase, cortisol, and ACTH) have been confirmed.

Furthermore, Vasoactive Intestinal Peptide (VIP) which is a living body activity hormone accelerates an intestinal peristalsis which is secreted from an alimentary canal, a pancreas, and a hypothalamus, and increases a blood flow including that of the alimentary canal etc. Moreover, vascularization and vascular permeability of microvessel are accelerated by a vascular endothelial growth factor (VEGF). It is considered that since the VIP and VEGF significantly increase by the "stress free treatment", both action of the VIP and that of the VEGF were induced, so that the blood flow of internal organs and peripheral blood flow were increased.

From these results, it is considered that with respect to sympathetic nerve activity through the autonomic nerves by the stress stimuli to a living body and overreaction of hypothalamohypophysial tropic hormones, the "stress free treatment" by thyroid stimulus acts on hypothalamus ascendence in an ascending manner, and while discharge of stress hormone is suppressed, the blood flow was increased through the VIP and VEGF.

Moreover, if a noxious stimulus such as stress and a pain is added to a living body, a finger tip cutis blood flow decreases, and a asympathetic flow response (SFR) appears. This reaction is evaluated by an index based on a peripheral blood flow as a reaction through a sympathetic nervous system against the noxious stimulus. In the stress free treatment, a blood flow at a central part of a wrist joint horizontal line increases, according to a laser Doppler tissue blood flowmeter, and it would appear that a reduction reaction of a blood flow, which mediates sympathetic flow response (SFR) by stress, increases a blood flow through the VIP and VEGF by the "stress free treatment" together with the depression effect of stress hormone.

Figure 2:
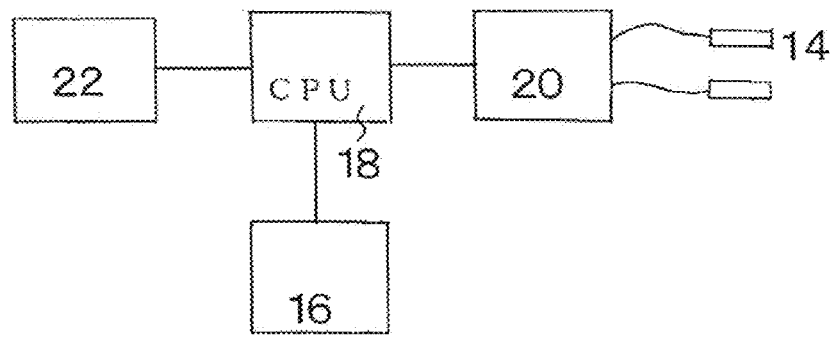
FIG. 2 is a schematic view of a circuit diagram of an electric type heating apparatus.

FIG. 1 is a schematic view of an electric type warm temperature heating apparatus used for the present invention. FIG. 2 is a schematic view of a circuit diagram of the electric type warm temperature heating apparatus.

A electric type warm temperature heating apparatus comprises the apparatus 10, and a guide element 14 for a thermal stimulus, which is connected to the apparatus 10 by a lead 12.

As shown, the apparatus 10 includes a memory unit 16, in which thermal stimulus patterns are stored, a control unit (CPU) 18, which reads out a thermal stimulus pattern from the memory unit 16, and an output unit 20, which supplies the thermal stimulus pattern to the guide element 14 for a thermal stimulus. A thermal stimulus is applied to a part to be stimulated, according to the thermal stimulus pattern.

A control unit (CPU) 18 is connected to the memory unit 16. A thermal stimulus pattern for obtaining a stimulus condition equivalent to that obtained from combustion of moxa is stored in the memory unit 16. The control unit (CPU) 18 reads out the thermal stimulus pattern from the memory unit 16, controls an output to a heating element(s) based on detection of a temperature sensor 22, and outputs the thermal stimulus pattern to the guide element(s) for a thermal stimulus.

The apparatus 10 is connected to two or more guide elements for a thermal stimulus in order to supply the thermal stimulus pattern to at least two different areas to be stimulated. In this manner, the thermal stimulus pattern is applied to the areas to be stimulated, through the guide elements for thermal stimulus.

A temperature sensor 22 is provided in a position(s) which is correlated with a temperature of an affected area near the heating elements. The guide elements for a thermal stimulus have a structure set forth below. The guide element 14 for a thermal stimulus, comprises a casing of apparatus 10, a heater which is provided in the casing, and is used as a source of warm temperature heating for applying thermal stimulus, a heat conduction board, which is provided on a lower face of the casing and which conducts heat of the heater to a skin of a patient, and a seal board provided on an upper face of the casing.

A heat conduction board of the guide elements for a thermal stimulus which are placed on two different areas, is desirably made up of at least two different kinds of metals. In this embodiment, aluminum and steel are used.

A temperature sensor is provided in a predetermined position of the housing which is in contact with a part of a human body, and detects the temperature of the position, so as to send a detection signal to a sensor amplifier. The control unit (CPU) controls an output of an electric power generating circuit so that the temperature of the portion, which is in contact with a skin surface of a human body contact, may not exceed a predetermined temperature. In the warm temperature heating apparatus, the surface temperature of the guide elements for a thermal stimulus is controlled so as to be in a range from 40 to 50±5 degrees Celsius.

When the heating temperature of the heating elements detected by the temperature sensor is equal to or lower than a reference temperature, a positive side period of a pulse signal is controlled so as to be long and a negative side period of the pulse signal is controlled so as to be short, according to the output of the temperature sensor. On the contrary, when it is in a state at the reference temperature, a positive side period is controlled so as to be short and a negative side period thereof is controlled so as to be long.

Figure 3:
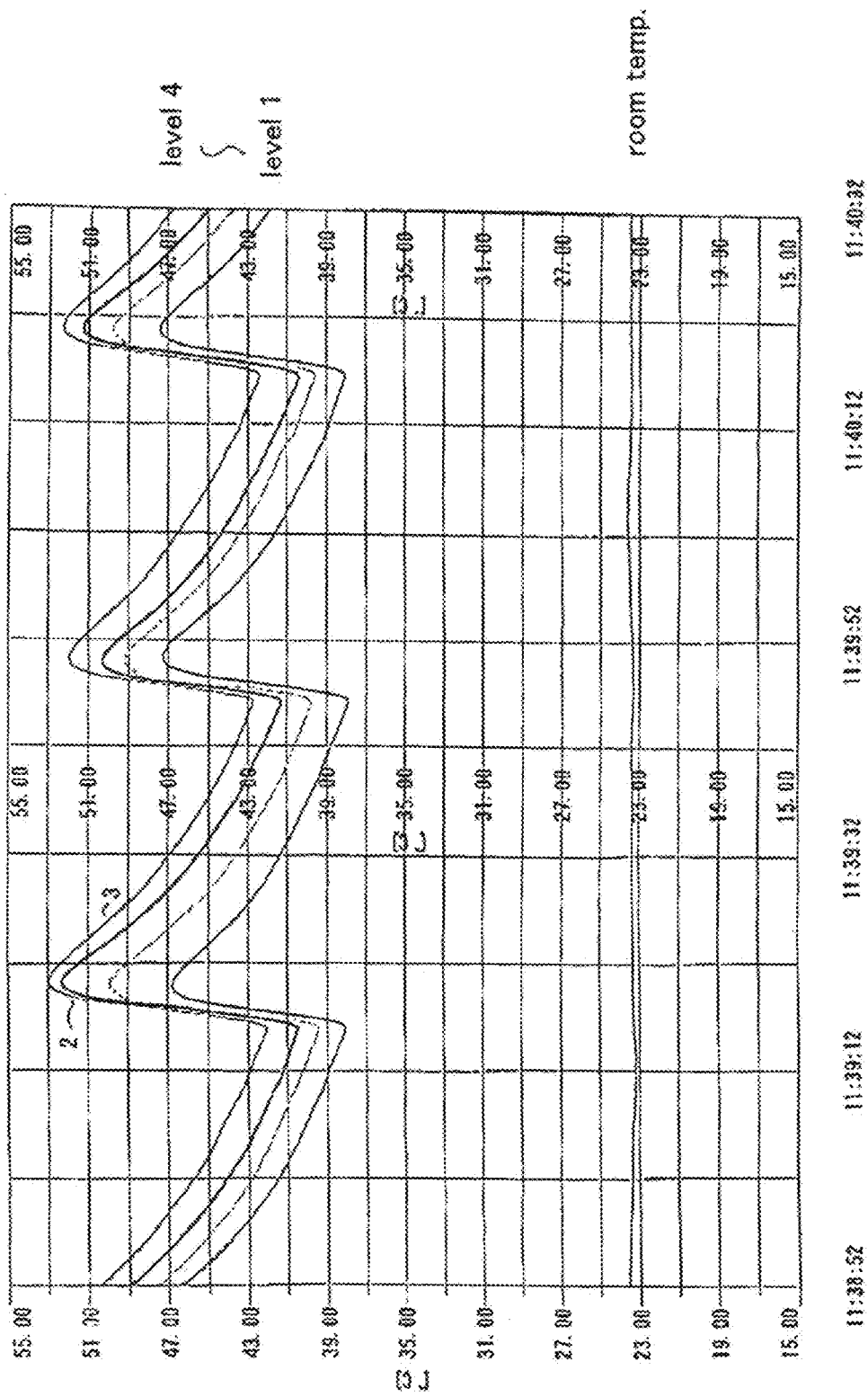
FIG. 3 is a schematic view of a thermal stimulus waveform obtained by controlling an electric type heating apparatus.

FIG. 3 shows a desirable thermal stimulus waveform, which is obtained by controlling the electric type warm temperature heating apparatus. The thermal stimulus waveform includes a heating waveform 2 obtained by heating it to a predetermined peak temperature, for example, 50±5 degrees Celsius, and a heat release waveform 3 which is formed by stopping heating after it reaches the peak temperature.

The heating waveform may be a convex shape heating waveform, an upward sloping line shape heating waveform, or a concave shape heating waveform. Moreover, the heating waveforms are not limited to the above-described heating waveform. It may be a saw-toothed shape waveform, and concavo-convex waveform. Moreover, the heating waveform and the heat release waveform may be formed as a sine waveform.

A cycle pattern of a thermal stimulus includes a thermal stimulus waveform made up of a warm heating waveform and a heat release waveform, and an interval before the next warm heating curve. One cycle pattern of the thermal stimulus is desirably set so that a thermal stimulus region may be 1 second to 30 seconds and an interval between the heating regions may be 1 second to 10 seconds.

The pattern of thermal stimulus desirably includes independent thermal stimulus waveforms whose phases are shifted so that the patterns of thermal stimulus do not substantially overlap each other. That is, as shown in the figures, the pattern of thermal stimulus includes a first thermal stimulus pattern including an interval between a thermal stimulus region and the next thermal stimulus region, and a second thermal stimulus pattern, which includes a thermal stimulus region during a certain period of an interval of the first thermal stimulus pattern and an interval in a first thermal stimulus region.

A cycle pattern of the thermal stimulus is desirably repeated for 10 minutes to 30 minutes. And, the cycle pattern of the thermal stimulus is desirably repeated again.

In addition, as a stimulus, an optical stimulus, a magnetic stimulus, an ultrasonic stimulus, a low frequency wave stimulus etc. may be used in addition to an acupuncture needle stimulus and a warm temperature heating stimulus.

Embodiment 1

Subjects were adult men and women. Burn injuries were taken into consideration so that an electric type warm temperature heating apparatus, MXA-8000 (SO-257), was used for a warm temperature heating stimulus. A probe thereof has a diameter of 10 mm, and a heating stimulus of warm temperature whose peak is 50±5 degrees Celsius was intermittently performed for 15 minutes. The probe was attached to the following warm temperature heating to the specific area to be stimulated of a body surface, and the specific areas was heated at 40 to 50 degrees Celsius.

Figure 4:
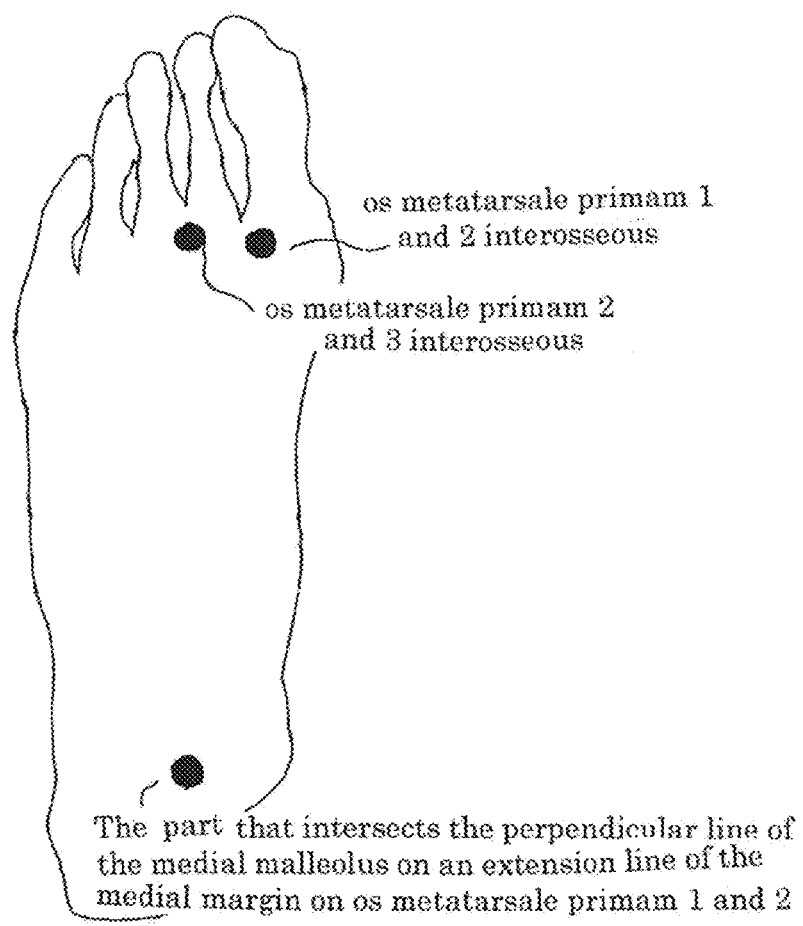
FIG. 4 is a schematic view of areas of a sole to be stimulated.

Here, the specific area to be stimulated is at least one selected from a group of os metatarsale primam 1 and 2 interosseous, os metatarsale primam 2 and 3 interosseous, or part that intersects the perpendicular line of the medial malleolus on an extension line of the medial margin on os metatarsale primam 1 and 2 in foot sole of right and left (refer to FIG. 4).

And a warm temperature heating stimulus is desirably applied to at least one specific area to be stimulated non-simultaneously and independently depending on the condition of disease.

Table 1 shows a result of blood flow measured at before and after of the stimulus at a central area of a wrist joint horizontal line by using a laser Doppler tissue blood flow meter, and the increase rate of blood flow. Wherein a warm temperature heating stimulus is applied at least one selected from a group of os metatarsale primam 1 and 2 interosseous, os metatarsale primam 2 and 3 interosseous, or part that intersects the perpendicular line of the medial malleolus on an extension line of the medial margin on os metatarsale primam 1 and 2 in foot sole of right and left as specific area to be stimulated.

TABLE 1

| Patient | stimulation before | stimulation after | increase rate |
|---|---|---|---|
| No. 1 | 1.287 | 2.1036 | 63 |
| No. 2 | 3.2791 | 8.0098 | 144 |
| No. 3 | 1.7603 | 2.959 | 68 |
| No. 4 | 2.8101 | 4.6872 | 68 |
| No. 5 | 5.9857 | 13.0065 | 117 |
| No. 6 | 3.453 | 6.9631 | 102 |
| No. 7 | 2.0954 | 4.7401 | 126 |
| No. 8 | 1.4332 | 3.5227 | 146 |
| No. 9 | 1.0091 | 1.7377 | 72 |
| No. 10 | 3.9592 | 8.0699 | 104 |
| No. 11 | 1.5635 | 3.8743 | 148 |

As shown in the Table 1, the effects of the treatment were remarkable when the increase rate of the blood flow was 60% or more, and preferably 100% or more. At least one specific area to be stimulated, which are different from each other, are selected. The increase rate of the blood flow is used as an indicator of the stimulus. The increase rate of the blood flow may be 60% or more, preferably, 100% or more. Also, the increase rate of the blood flow is used as an indicator in evaluation of the stimulus.

Taking into consideration influences on the psychological stress through autonomic nerves, after keeping the subjects at rest in a state of a dorsal position for 20 minutes, the blood pressure, core body temperature, salivary amylase, and HEARTRATER (artery age) are measured and a warm temperature stimulus is performed just for 15 minutes, and they are measured again immediately after the stimulus.

Figures 5, 6:
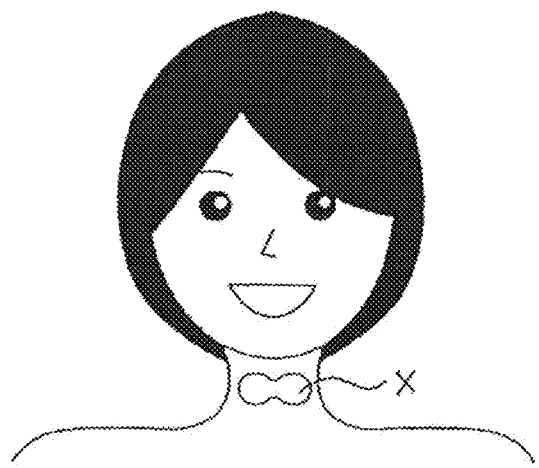
FIG. 5 is a schematic view of a protocol of a thermal stimulus.
FIG. 6 is a schematic view of an area near a thyroid gland to be stimulated.

The protocol of thermal stimulus is shown in FIG. 5. A treatment is made for the one time and the above-mentioned measurement is carried out before and after the treatment and next day thereto. A precapillary circulation which is innervated by an autonomic nervous system was measured by a deep body thermometer (a deep body temperature monitor, CORE TEMP CM-210 manufactured by TERUMO CORP.), and psychological stress is measured by DAEKI AMY (a salivary amylase monitor manufactured by NIPRO). Furthermore, an arteriosclerosis index and blood vessel age are quantified by HEARTRATER.

Blood is collected twice, that is, before the stimulus and at the same time one day after the stimulus, and a subject is refrained from consuming any food or liquid, except for water after 9:00 PM one day before the test and the test day. Moreover, an advance explanation is made so that they refrain from undertaking strenuous forms of exercise from 24 hours before the test to one day after the test, and instructions are given to them to use a vehicle from home to a laboratory on the morning of the test day if possible, and to avoid intense activity and travel with minimum action.

It was observed that temperature rises in the area to be stimulated. It is noted that an increase in temperature was 2.1, especially when the stimulus was applied to os metatarsale primam 2 and 3 interosseous. As to salivary amylase, an increase tendency was shown when the stimulus was applied to os metatarsale primam 2 and 3 interosseous. The salivary amylase increase +34.25. Moreover, the cortisol is decreased −3.33 at os metatarsale primam 1 and 2 interosseous, and is decreased −6.33 at part that intersects the perpendicular line of the medial malleolus on an extension line of the medial margin on os metatarsale primam 1 and 2, When stimulus was applied to os metatarsale primam 1 and 2 interosseous, a significant decrease of systolic arterial pressure was −13.00.

When a stimulus was applied to os metatarsale primam 1 and 2 interosseous, a total cholesterol significantly is decreased −10.33. The neutral fat also is decreased −24.67 at part that intersects the perpendicular line of the medial malleolus on an extension line of the medial margin on os metatarsale primam 1 and 2. As to A.I. (arteriosclerotic index), when a stimulus was applied to to os metatarsale primam 1 and 2 interosseous, A.I. is decreased −0.10.

When a stimulus was applied to the area located at os metatarsale primam 1 and 2 interosseous; or os metatarsale primam 2 and 3 interosseous, the blood sugar level is decreased by −5.33 or 5.25. Furthermore, a hemoglobin A1c also decreased −0.13, when a stimulus was applied to os metatarsale primam 2 and 3 interosseous.

The amount of secretion of gastrin which is a gastrointestinal hormone was significantly increased 19.33 or 48.67, when a stimulus was applied to an os metatarsale primam 2 and 3 interosseous or part that intersects the perpendicular line of the medial malleolus on an extension line of the medial margin on an os metatarsale primam 1 and 2. This suggests that the digestive absorption and an intestinal peristaltic motion etc. increased.

When a stimulus was applied to an os metatarsale primam 1 and 2 interosseous, an Adiponectin is increased +1.5. Since the Adiponectin is considered as one of the substances which activates Sirtuin gene, and is one of genes relating to a long life, it was suggested that two stimuli to two areas of the plantar part turned ON the gene related to a long life.

When a stimulus is applied to an os metatarsale primam 1 and 2 interosseous, or part that intersects the perpendicular line of the medial malleolus on an extension line of the medial margin on os metatarsale primam 1 and 2, the leptin is decrease −0.57 or −0.20. The leptin is called "starvation hormone", and a body can originally store fat in the body. It is said that at the present day, 95% of cause of obesity is caused by "leptin resistance" due to excess leptin. It is thought that the Dayez effect would be expected by adjusting the amount of secretion of this substance.

A balance of an autonomic nerve is measured by Heart regulator. A degree of an activity of an autonomic nerve is increased +28.33 at an os metatarsale primam 1 and 2 interosseous. A degree of a resistance of an autonomic nerve is increased +14.67 at os metatarsale primam 1 and 2 interosseous or +12.25 at os metatarsale primam 2 and 3 interosseous. An index of a stress is decreased −17.00 at an os metatarsale primam 1 and 2 interosseous. A degree of a fatigue is decreased −30.00 at an os metatarsale primam 1 and 2 interosseous.

Embodiment 2

In this embodiment, an example which gave the acupuncture needle stimulus was applied to an area near thyroid gland as the specific area to be stimulated (refer to FIG. 6). The thyroid gland is an internal organ which is located in a shallow position from the body surface, and is observed at the depth in a range of approximately 5 mm-30 mm. Therefore, in general, an examination is performed by using a high frequency superficial probe in an ultrasonographic examination. The long diameter of the thyroid gland is approximately 40-50 mm, the thickness thereof is approximately 12-18 mm, the width diameter thereof is approximately 15-25 mm, and the thickness of isthmus thereof is approximately 2-4 mm.

The Acupuncture was performed for a total of ten men and women between the ages of 20 and 60 years old who have diagnosed as high blood pressure. Expecting influence action to psychological stress which is mediated by autonomic nerves, a disposable acupuncture needle (which was made of stainless steel, was 40 mm in length, and was thickness of 0.18 mm) was inserted to anterior neck region at a depth of 2-3 cm. After keeping subjects, who were examined, at rest in a state of a dorsal position for 15 minutes, blood pressure, core body temperature, and salivary amylase thereof were measured. And then the acupuncture needle stimulus was applied to them for 15 minutes, and they were measured again immediately after the needle was got out. The treatment was performed seven times, that is, 3 days after the first day, 7 days thereafter, 10 days thereafter, 14 days thereafter, 17 days thereafter, 21 days thereafter, In EMBODIMENT 2, the blood flow may be measured at before and after of the stimulus at a central area of a wrist joint horizontal line by using a laser Doppler tissue blood flow meter. And the same result as Table 1 of EMBODIMENT 1 may be obtained.

Effects

Values of alivary amylase, the highest and the lowest blood pressure showed significant decreased by the acupuncture needle stimulus. On the other hand, the core body temperatures at distances of 3 mm and 5 mm also showed the significant rise.

As for the salivary amylase, a increase was observed in +35. It is thought that since there were subjects who always had a high psychological stress among subjects with hypertension, the removal thereof decreased the pressure. There was a tendency in which systolic arterial pressure and diastolic blood pressure of the subjects decreased −13, when the acupuncture treatment continued. It was observed that subjects to whom hypotensor is not administered, rise in blood pressure immediately after the acupuncture treatment. Subjects, who were low in core body temperature at distances of 3 mm and 5 mm, greatly rose in the deep core temperature +2, and it was observed that the core body temperature converged at normal body temperature on the whole. Moreover, there was a tendency in which core body temperature before the acupuncture treatment became high, when the acupuncture treatment continued.

When the acupuncture treatment continued, the amount of secretion of cortisol and further that of ACTH which was a higher center thereof, decreased remarkably, immediately after the acupuncture needle treatment was performed on zero day, It was observed that it decreased after going up gently thereafter. Although the cortisol and ACTH of all the subjects transiently decreased, immediately after the acupuncture needle treatment was performed, and then the gradual increase tendency was shown, it was observed that there was a tendency in which it decreased when the treatment continued.

It was shown that there was a tendency to gently decrease in T-CHOL, HDL-CHOL, and LDL-CHOL.

Embodiment 3

In this embodiment, moxa cautery was performed on an area between an outer skin and a horizontal line on a inner border part of hallux distal phalanx bottom of left and/or right foot and phalanx proximalis in foot sole of right and left as a specific area to be stimulated.

Figure 7:
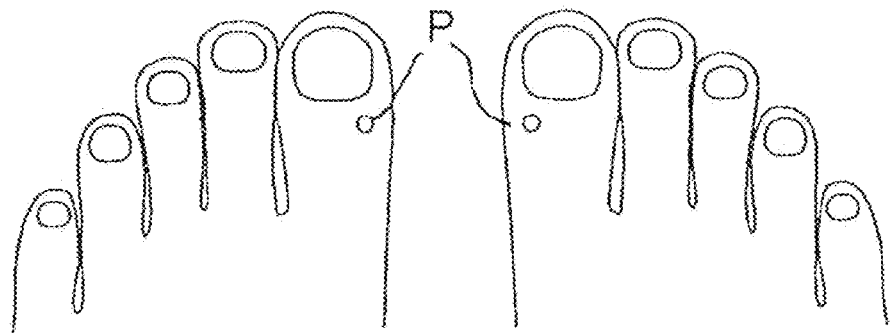
FIG. 7 is a schematic view of an area of a toe of a leg to be stimulated.

In FIG. 7, a symbol "∘" shows a specific area to be stimulated between the outer skin and a horizontal line of the inside boundary part of a hallux distal phalanx bottom and a proximal phalanx bone head, and applies a stimulus.

The moxa was applied to subjects by using pre-rolled moxa. The moxibustion was continuously performed five times respectively area between the outer skin and a horizontal line of the inside boundary part of a hallux distal phalanx bottom and a proximal phalanx bone head, and applies a stimulus.

The quantity of moxa per one moxibustion is 0.002 g, and the combustion temperature was 80±5 degrees Celsius at maximum. Two sets of treatments, which were performed in the beginning of week and the end of week, were repeated three times, that is, the treatment was performed six times in total.

It was confirmed from clinical data that secretion of thyroid hormone was activated by applying stimulus to area between the outer skin and a horizontal line of the inside boundary part of a hallux distal phalanx bottom and a proximal phalanx bone head, and applies a stimulus.

In EMBODIMENT 3, the blood flow may be measured at before and after of the stimulus at a central area of a wrist joint horizontal line by using a laser Doppler tissue blood flow meter. And the same result as Table 1 of EMBODIMENT 1 may be obtained.

Thereby, a rise in core body temperature, and prevention and improvement of obesity, diabetes, etc is achieved. Therefore, it is thought that the treatment is one of the effective ways for a therapeutic procedure to lifestyle-related diseases, such as diabetes and obesity. Especially, explanation will be given below with respect to clinical data of a rise in core body temperature, diabetes and obesity on which remarkable effects were shown.

It was performed for a total of nine men and women between the ages of 20 and 60 years old who have diagnosed as diabetes, obesity and high blood pressure. Stimulation was applied by moxibustion to parts between the outer skin and the horizontal line of an inner border of hallux distal phalanx bottom of left and/or right foot and phalanx proximalis.

As described above, there are effects of a rise in core body temperature, a reduction of neutral fat, a reduction of cholesterol, a reduction of insulin, and suppression of arteriosclerosis.

It is preferred to perform the stimulus treatment to least one of the specific area to be stimulated selected from a group of EMBODIMENT 1 or EMBODIMENT 2 or The preceding description has been presented only to illustrate and describe exemplary embodiments of the present stimulus method for releasing stress, and stress-free medical treatment method by the stimulus method. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope.

Embodiment 4

Figure 8A:
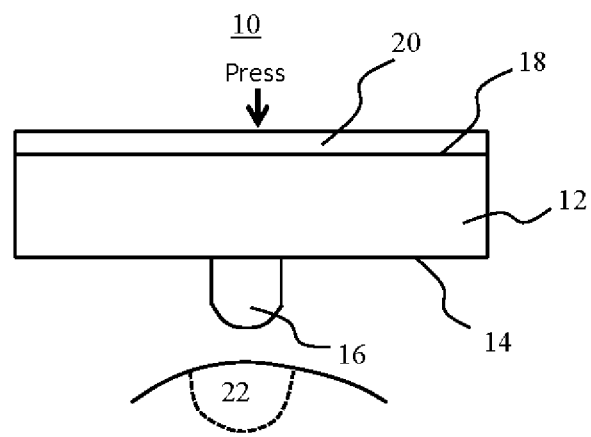
FIGS. 8A and 8B show a stimulation application apparatus according one embodiment of the present application.
Figure 8B:
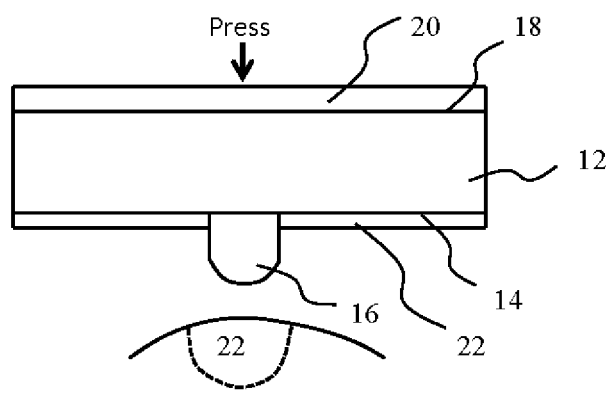

FIG. 8 shows a cross-sectional view of the stimulation application apparatus utilized in the present embodiment. The stimulation application apparatus 10 has a substrate 12 provided with an elastic member, a stimulation application member 16 provided on a first surface 14 of the substrate 12 which will be in contact with a site of a body to be stimulated, and a stimulation imposition layer 20 provided on a second surface 18 of the substrate 12 and configured to impose the stimulation applied to the stimulation application member 16.

The stimulation used by the apparatus is preferably heat and/or pressure applied to the site. Preferably, the first surface of the substrate is provided with an adhesive member 22 which attaches and fixes the stimulation application member to the site. Preferably, the substrate includes a material selected from a silicone rubber material, a mixture of silicone rubber and a thermally conductive member, and a mixture of silicone rubber and a magnetic material. Preferably, the substrate has a porous structure in which a drug or agent can be placed. Preferably, the stimulation imposition layer 20 has a thin layer made of ceramics or metal.

The stimulation application member preferably has a material with a high thermal conductivity and/or a heat-retaining effect. The stimulation application member comprises any one selected from gold, platinum, iron, diamond, a carbon material, rubber, a composite of metal and a carbon material, a composite of a resin and a carbon material, and a composite of rubber and a foam material.

Figure 9B:
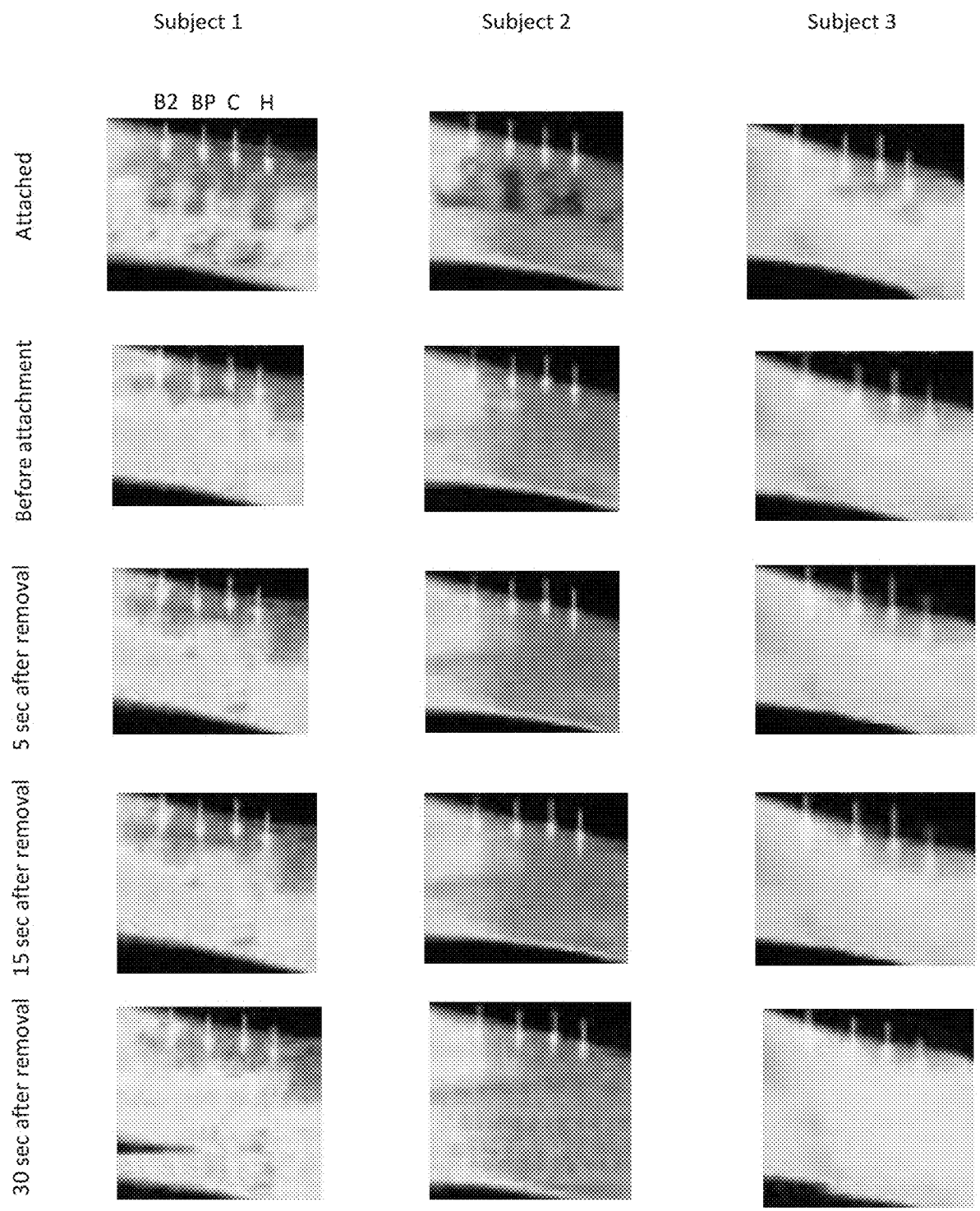

FIGS. 9A and 9B are photographic data showing a comparative test on heat-retaining effects by samples, including: (H) HELICAL (a carbon-made micro-coil); 1.5 mm thickness: (C) polychloroprene rubber; 1.5 mm thickness: (BP) butyl rubber+polyethylene foam; 1.5 mm thickness: and (B2) butyl rubber; 1.5 mm thickness.

FIG. 9B shows the results of the heat-retaining comparative test captured by a thermographic camera. Pairs of each sample were applied to a front side of dorsal upper arms of three subjects by using surgical tapes and retained for five minutes. The images show temperature distributions captured over time after the samples were removed. It was observed in all the three subjects that the butyl rubber+polyethylene foam (BP) was the most effective material to increase the skin surface temperature right after the removal of the samples. The skin temperature increased by 1° C. and the increased temperature lasted for about 30 seconds after the removal of the sample. In FIG. 9B, red in color represents portions with the highest temperature and the temperature decreases as the color changes from red to green. It was also observed in all the three subjects that the butyl rubber+polyethylene foam (BP) was the most heat-inclusive material. Thus, the butyl rubber+polyethylene foam (BP) is assumed to be the most effective material to retain heat of the skin where it is applied to among the other materials. In particular, it was shown that the skin surface temperature of the front side of dorsal upper arm of Subject 3 was increased in its entirety, and the second effective result was observed on the skin surface temperature of the front side of dorsal upper arm of Subject 2 which was also increased in its entirety.

In view of the above results, a preferable material to be applied to the site to be stimulated is a material formed with a combination of butyl rubber sheet or silicon rubber sheet with about 1.5 mm thickness and polyethylene foam or urethane foam with about 0.5 mm, and preferably, such material is shaped in a disc having about 5 mm diameter for use.

The polyethylene foam or urethane foam is used on the side to be attached to the skin to maximize the heat-retaining effect. Since the polyethylene foam or urethane foam do not contain nature-occurring organic substances, these materials are preferably used as allergen-free materials. Further, these materials are preferable because they have a certain degree of hardness required to apply a pressure, while it is possible to retain the heat-insulation effect.

The stimulation application member 16 is preferably shaped in a disc, conical, or rectangular parallelepiped, with a diameter of about 2 to 4 mm, and a height of about 2 to 3 cm.

It is preferable to provide a stimulation imposition layer on the substrate for imposing the stimulation on the stimulation application member. However, a stimulation imposition layer may not be required when the substrate and the stimulation application member are made of a material with a high degree of hardness.

The stimulation application site 22 includes at least one area selected from a group of (F) site that intersects the perpendicular line of the medial malleolus on an extension line of the medial margin on os metatarsale primam 1 and 2 in foot sole, and (L) incisurasive foramen supraorbitalis site, and (K) site where the lintersection of the line connecting an augulus oculi medialis of eye and L site, and perpendicular of an augulus oculi lateralis of eye is located, and (M) site of augulus oculi lateralis located above 1 horizontal finger from center of the line where connect the inner end of left and right eyebrow. However, the stimulation site may not be limited to the above sites, and it may include other sites effective to increase a blood flow by 60% or more after the application of the stimulation, as compared to the blood flow before the application of the stimulation.

A method of applying stimulation according to the above embodiment includes a step of providing a stimulation application apparatus comprising a substrate, a stimulation application member provided to a first surface of the substrate and configured to be in contact with a site of a body to be stimulated, and a stimulation imposition layer provided to a second surface of the substrate opposed to the first surface and configured to impose the stimulation applied to the site via the stimulation application member, a step of bringing the stimulation application member of the stimulation application apparatus into contact with the site to be stimulated and fixing the stimulation application member to the site, and a step of pressing the stimulation imposition layer on the site to be stimulated to impose the stimulation and applying the imposed stimulation to the site via the stimulation imposition layer.

It is preferred to heat the stimulation application member with a heating device. It is preferred to apply a pressure to the stimulation application member, with a force applied to the stimulation imposition layer. When the stimulation application apparatus is used, the stimulation application member is contacted with and fixed to the stimulation application site. The stimulation application member is attached with an adhesive member provided to the first surface of the substrate, thereby mounting the apparatus thereto. By pressing the upper surface of the stimulation imposition layer with a hand, the impose stimulus force is applied to the stimulation application site though the stimulation application member. In this manner, the stimulation application apparatus and method according to the present invention can effectively increase the blood flow.

The invention claimed is:

1. A method of applying stimulation, comprising the steps of:

applying a stimulation application member of a stimulation application apparatus on a site of a body, wherein the stimulation application apparatus comprises: a substrate which comprises a material selected from the group consisting of butyl rubber, a silicon rubber, polychloroprene rubber, polyethylene, urethane, and a combination of the butyl rubber or the silicon rubber with the polyethylene or the urethane; the stimulation application member comprising a combination of rubber and heat-retaining material and provided on a first surface of the substrate, the heat-retaining material being placed on a side which directly contacts the site of the body; and a stimulation imposition layer comprising a ceramic or metal and provided on a second surface of the substrate opposed to the first surface;

heating the stimulation application member being applied on the site, and applying a force and heat to the stimulation imposition layer such that the stimulation comprising both heat and pressure is applied to the site via the stimulation application member, wherein the site comprises (1) (F) site that intersect the perpendicular line of the medial malleolus on an extension line of the medial margin on OS metatarsale primam 1 and 2 in foot sole, and (2) at least one selected from a group consisting of (L) incisurasive foramen suprorbitalis site and (K) site that the litersection of the line connecting an augulus oculi medialis of eye and (M) site of augulus oculi lateralis located above 1 horizontal finger from center of the line where connect the inner end of left and right eyerom, such that a blood flow increases at 60% or more as compared to the blood flow before the application of the stimulation.

2. The method according to claim 1, wherein the stimulation application member applied to the site of the body comprises a composite of butyl rubber and polyethylene foam.

3. The method according to claim 1, wherein the heat-retaining material is a foam material.

4. A method of applying stimulation, comprising the steps of:

applying a stimulation application member of a stimulation application apparatus on a site of a body, wherein the stimulation application apparatus comprises: a substrate which comprises a material selected from the group consisting of butyl rubber, a silicon rubber, polychloroprene rubber, polyethylene, urethane, and a combination of the butyl rubber or the silicon rubber with the polyethylene or the urethane; the stimulation application member comprising a combination of rubber and heat-retaining material and provided on a first surface of the substrate, the heat-retaining material being placed on a side which directly contacts the site of the body; and a stimulation imposition layer comprising a ceramic or metal and provided on a second surface of the substrate opposed to the first surface;

heating the stimulation application member being applied on the site, and applying a force and heat to the stimulation imposition layer which comprises the ceramic or metal such that the stimulation comprising both heat and pressure is applied to the site via the stimulation application member, wherein the site comprises (1) (F) site that intersect the perpendicular line of the medial malleolus on an extension line of the medial margin on OS metatarsale primam 1 and 2 in foot sole, and (2) at least one selected from a group consisting of (L) incisurasive foramen suprorbitalis site and (K) site that the litersection of the line connecting an augulus oculi medialis of eye and (M) site of augulus oculi lateralis located above 1 horizontal finger from center of the line where connect the inner end of left and right eyerom, such that a blood flow increases at 60% or more as compared to the blood flow before the application of the stimulation, and wherein the material of the substrate, the composite of rubber and heat-retaining material of the stimulation application member and the ceramic or metal of the stimulation imposition layer are used to apply to the force to the site of the body.

5. The method according to claim 4, wherein the stimulation application member applied to the site of the body comprises a composite of butyl rubber and polyethylene foam.

6. The method according to claim 4, wherein the heat-retaining material is a foam material.

* * * * *